United States Patent [19]

Pisharodi

[11] Patent Number: 5,653,761
[45] Date of Patent: Aug. 5, 1997

[54] METHOD OF LUMBAR INTERVERTEBRAL DISK STABILIZATION

[76] Inventor: Madhavan Pisharodi, 844 Central Blvd., Ste. 1200, Brownsville, Tex. 78520

[21] Appl. No.: 471,910

[22] Filed: Jun. 7, 1995

Related U.S. Application Data

[62] Division of Ser. No. 210,229, Mar. 18, 1994.

[51] Int. Cl.⁶ ..................... A61F 2/44
[52] U.S. Cl. ............. 623/17; 623/66; 606/61; 606/60; 606/63
[58] Field of Search .......... 623/17, 66; 606/60, 606/61, 62, 63, 66, 73, 53

[56] References Cited

U.S. PATENT DOCUMENTS

| | | | |
|---|---|---|---|
| 3,334,624 | 8/1967 | Schneider et al. | 606/62 |
| 3,486,505 | 12/1969 | Morrison | 128/303 |
| 4,349,921 | 9/1982 | Kuntz | 623/17 |
| 4,657,550 | 4/1987 | Daher | 623/17 |
| 4,711,232 | 12/1987 | Fischer et al. | 128/92 |
| 4,759,769 | 7/1988 | Hedman et al. | 623/17 |
| 4,834,757 | 5/1989 | Brantigan | 623/17 |
| 4,863,476 | 9/1989 | Shepperd | 623/17 |
| 4,932,975 | 6/1990 | Main et al. | 623/17 |
| 5,015,247 | 5/1991 | Michelson | 606/61 |
| 5,059,193 | 10/1991 | Kuslich | 606/61 |
| 5,171,278 | 12/1992 | Pisharodi | 623/17 |
| 5,306,309 | 4/1994 | Wagner et al. | 623/17 |
| 5,324,292 | 6/1994 | Meyers | 606/73 |
| 5,443,514 | 8/1995 | Steffee | 623/17 |
| 5,549,679 | 8/1996 | Kuslich | 623/17 |

FOREIGN PATENT DOCUMENTS

| | | |
|---|---|---|
| 0042271 | 12/1981 | European Pat. Off. . |
| 0260044 | 3/1988 | European Pat. Off. . |
| 0307241 | 3/1989 | European Pat. Off. . |
| 3505567 | 6/1986 | Germany . |
| 3729600 | 3/1989 | Germany . |
| 0662082 | 2/1982 | U.S.S.R. . |
| WO9214423 | 9/1992 | WIPO . |

*Primary Examiner*—Paul B. Prebilic
*Attorney, Agent, or Firm*—Mark R. Wisner

[57] ABSTRACT

A method of intervertebral disk stabilization in which adjacent vertebrae are spread and a portion of the intervertebral disk is removed from therebetween is disclosed. An elongate, generally cylindrically shaped implant having middle and end portions, the middle portion being of larger diameter than the end portions, is inserted into the space between the adjacent vertebrae from which the disk was removed and then rotated. Threads formed on the outside surface of the implant bear against the bodies of the adjacent vertebrae to move the implant back and forth in an anterior-posterior direction in the disk space to a position in which both the larger diameter middle portion and the smaller diameter end portions of the implant engage the bodies of the adjacent vertebrae to stabilize the adjacent vertebrae relative to each other.

16 Claims, 6 Drawing Sheets

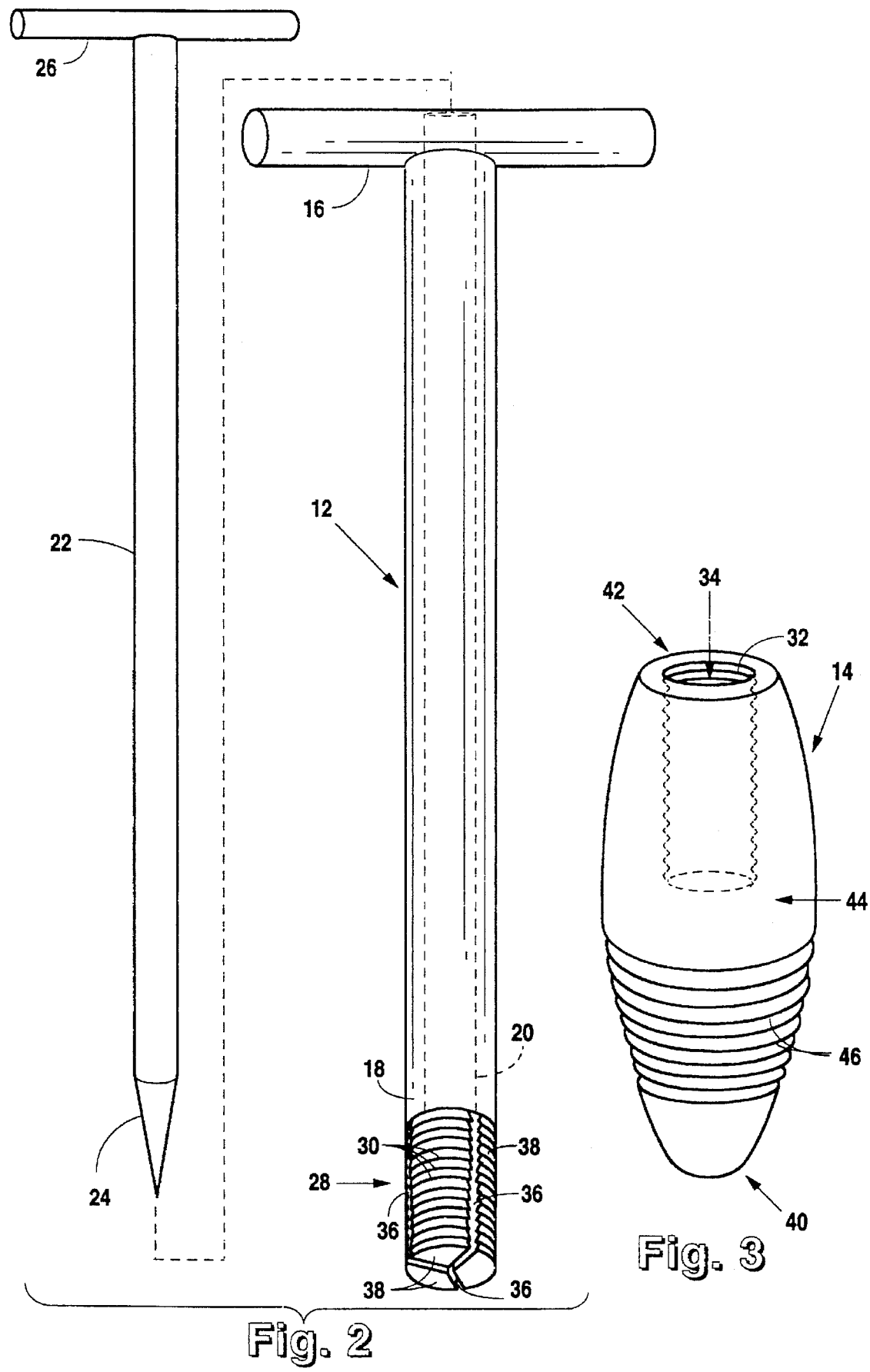

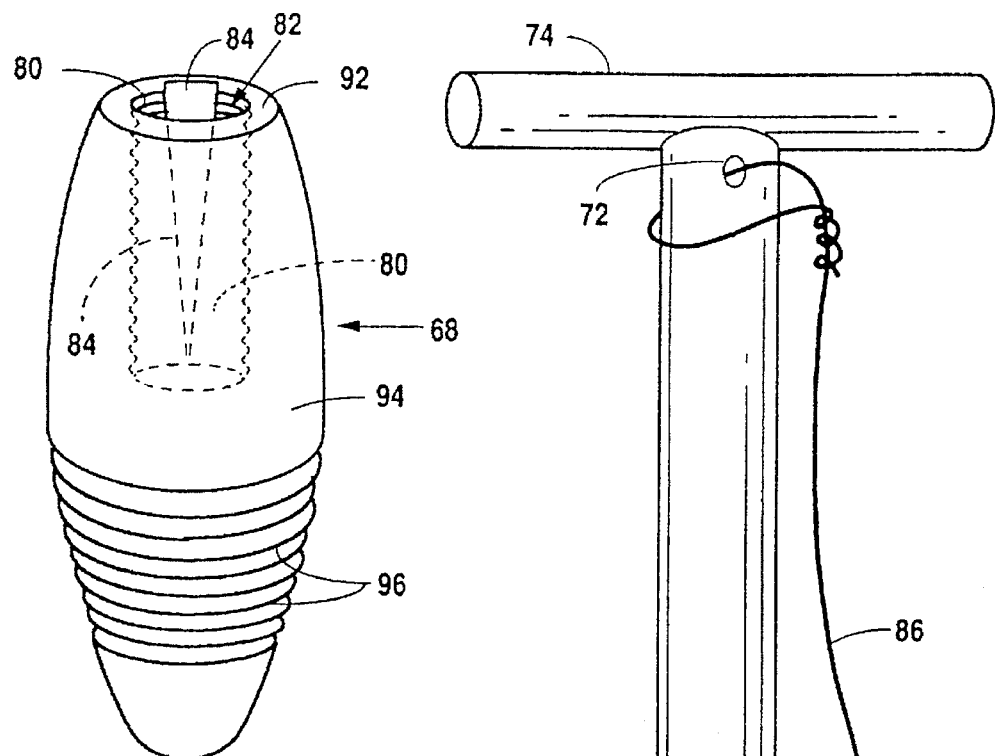
Fig. 8
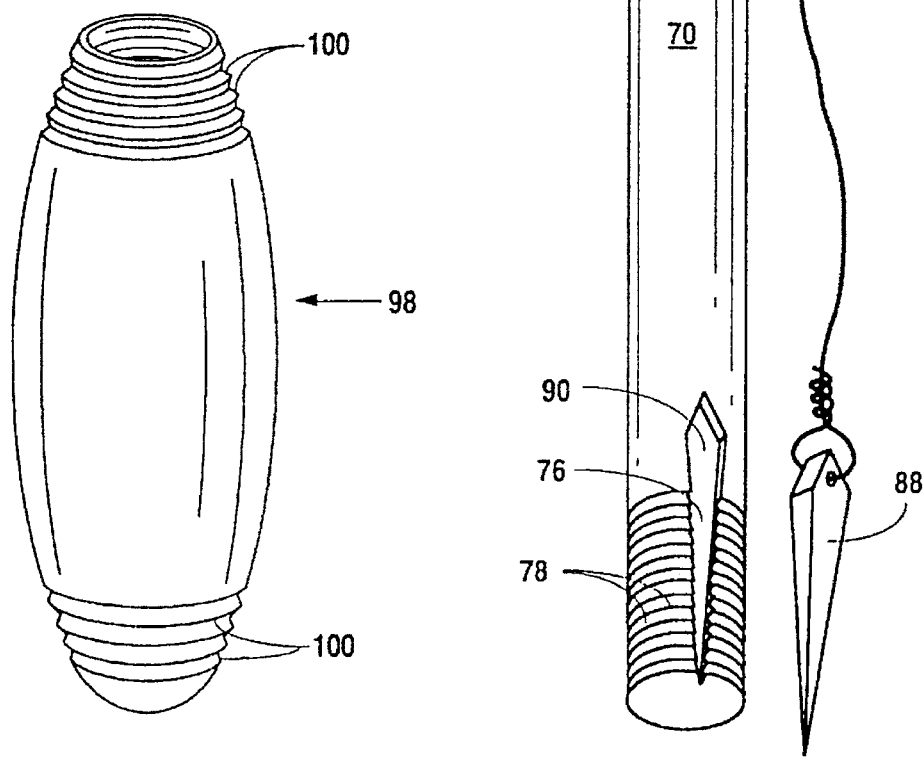
Fig. 10
Fig. 7

METHOD OF LUMBAR INTERVERTEBRAL DISK STABILIZATION

This application is a divisional of co-pending application Ser. No. 08/210,229, filed Mar. 18, 1994.

BACKGROUND OF THE INVENTION

The present invention relates to an intervertebral disk stabilizing implant and a method of lumbar intervertebral disk stabilization ("LIDS"). More specifically, the present invention relates to cylindrically shaped disk implants which are expanded in the middle portion which are used for spinal fusion.

The spine is a flexible structure comprised of thirty-three vertebrae separated and cushioned from each other by fibrous intervertebral disks. If the spine is injured or becomes diseased, surgical intervention involving removal of one or more disks, and fusion of the adjacent vertebrae, may be indicated. The more frequent injuries are in the lower lumbar and in the lower cervical regions.

Treatment of a herniated disk in the neck and in the lumbar region continues to be a challenging field of medicine. The classical treatment for a ruptured disk continues to be diskectomy, i.e., removal of the disk from between the vertebrae. In this process, all or a portion of the interverte- bral disk is removed, leaving a defect which continues to bother the patients throughout the rest of their lives. An additional procedure is to replace the disk space with a bone graft, usually bone chips cut from the patient's iliac crest, bringing about fusion of the vertebrae above and below the disk, eliminating the empty space between the vertebrae.

Theoretically, a diskectomy with fusion is a satisfactory procedure, though not ideal because the replaced bone does not have any of the functions of the cartilaginous tissue of the disk, i.e. no cushioning effect, and has complications because of several factors. First, conventional bone plugs used to pack the disk space do not conform to the shape of the disk because the disk bulges maximally in the center. The disk space is wider in the middle and narrower at its anterior and posterior ends. For this reason, the various bone plugs which are currently available commercially have only four contact points, i.e. at the front and back of the disk space. Secondly, access to the disk is from one side or the other of the dorsal spine of the adjacent vertebrae, leaving a space that is "off-center" relative to the bodies of the adjacent vertebrae. An implant inserted into that off-center space, therefore, replaces only a portion of the disk and consequently contacts only a portion of the bodies of the adjacent vertebrae such that the stability of the implant is even more problematical than might be apparent from the limited contact resulting from the shape of the intervertebral space in the first place. Another complication is the possibility of infection or other conditions which may require the removal of the implant. Also, if the bone pieces do not fuse, they may eventually extrude out of the disk space, causing pressure on the nerve roots.

Various prosthetic disk plugs, or implants, are disclosed in the art, but all are characterized by limitations of not conforming to the shape of the disk space, lack of stability when inserted off-center, inability to be removed, or other disadvantages. For instance, U.S. Pat. No. 4,863,476 describes an elongated body divided longitudinally into two portions having a cam device movable therebetween for increasing the space between the two body portions once inserted into the disk space. However, that device is generally cylindrical in shape such that the only contact points between the device and the vertebral bodies are at the front and back of the disk space, creating increased likelihood of instability and generally rendering that device unsuitable for use after partial diskectomy. The art also discloses intervertebral disk prostheses (e.g., U.S. Pat. Nos. 3,867,728, 4,309, 777, 4,863,477 and 4,932,969 and French Patent Application No. 8816184) which may have more general contact with the adjacent disks, but which are not intended for use in fusion of the disks. The art also includes spinal joint prostheses such as is described in U.S. Pat. No. 4,759,769, which is again not indicated for use when fusion is the preferred surgical intervention.

There is, therefore, a need for a device capable of stabilizing the vertebrae adjacent an intervertebral disk, but which is also removable, for use in spinal fusion. There is also a need for a method of implanting such a stabilizer.

SUMMARY OF THE INVENTION

These needs are met in the present invention by providing a vertebral disk stabilizer comprised of a generally cylindrical, elongate implant having end and middle portions, the middle portion having a diameter larger than the diameter of the end portion, threads formed on the outside surface of the implant for bearing against the bodies of the adjacent vertebrae when the implant is inserted into the anatomical region from which a portion of the intervertebral disk has been removed, and an applicator. The applicator is mounted to the implant for (1) facilitating the insertion of the implant into the region between the adjacent vertebrae from which the portion of the disk has been removed and (2) rotating the implant so as to cause the implant to move in an anterior-posterior direction as the threads bear against the bodies of the adjacent vertebrae to a position in which both the middle and end portions of the implant engage the bodies of the adjacent vertebrae so as to more completely support the upper vertebrae, thereby stabilizing the adjacent vertebrae, and is subsequently detached therefrom.

Also provided is a method of stabilizing adjacent vertebrae, particularly lumbar vertebrae, Comprising the steps of spreading two adjacent vertebrae and removing a portion of the intervertebral disk from therebetween, followed by insertion of an elongate, generally cylindrically shaped implant having middle and end portions, the middle portion being of larger diameter than the end portion, into the space between the adjacent vertebrae from which the disk has been removed. The implant is then rotated to cause threads formed on the outside surface thereof to bear against the bodies of the adjacent vertebrae to move the implant in an anterior-posterior direction until positioned at a point between the adjacent vertebrae at which both the larger diameter middle portion and the smaller diameter end portion of the implant engage the vertebrae to stabilize the adjacent vertebrae relative to each other.

BRIEF DESCRIPTION OF THE DRAWINGS

FIG. 2 is a projected view of the applicator of the stabilizer of FIG. 1 after being detached from the implant.

FIG. 3 is a projected view of the implant of the stabilizer of FIG. 1 after being detached from the applicator.

FIG. 7 is a projected view of the applicator of the stabilizer of FIG. 6 after detaching the implant therefrom.

FIG. 8 is a projected view of the implant of the stabilizer of FIG. 6 after being detached from the applicator.

FIG. 10 is a projected view of another embodiment of an implant constructed in accordance with the present invention and which is used in place of the implant of FIG. 3.

DETAILED DESCRIPTION OF THE PREFERRED EMBODIMENT

Figure 1:
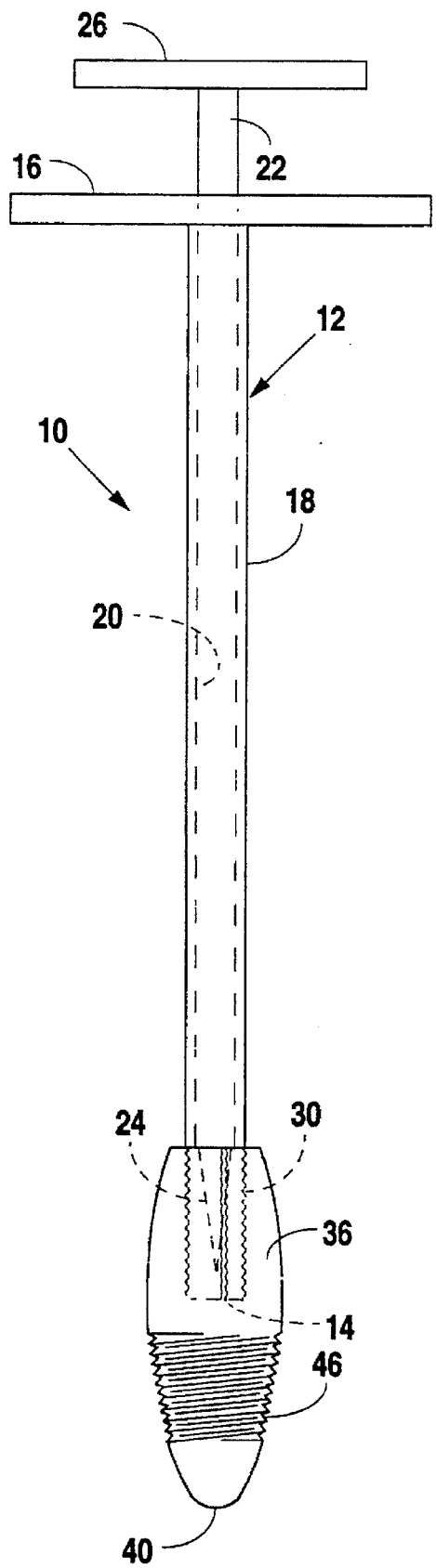
FIG. 1 is a plan view of a preferred embodiment of a vertebral disk stabilizer constructed in accordance with the present invention.

Referring now to the figures, multiple embodiments of the present invention will be illustrated and described in more detail. Specifically with regard to the embodiment shown in FIG. 1, the stabilizer is indicated generally at reference numeral 10, and is comprised of two parts, an applicator 12 and an implant 14. Applicator 12 is shown with a handle 16 in the shape of a "T", but it will be recognized from this disclosure by those skilled in the art that the handle 16 may take the form of any convenient hand grip or other structure which facilitates the handling of the stabilizer 10 and subsequent rotation of the stabilizer 10 once the implant 14 has been inserted into the space between two adjacent vertebrae as more particularly described below.

As shown more clearly when FIG. 1 is viewed in conjunction with FIGS. 2 and 3, applicator 12 is comprised of an elongate mandrel 18 having a longitudinal bore 20 therethrough, the bore 20 terminating in a point, with an elongate piston 22 disposed therein. Piston 22 is provided with a wedge-shaped, or pointed, end 24 which is sized to approximate the shape of the pointed end of the bore 20 in mandrel 18 at one end and a handle 26 formed at the other end. As best shown in FIG. 2, the end 28 of mandrel 18 is provided with screw threads 30 which mate with the threads 32 (see FIG. 3) formed in the interior wall of the bore 34 in implant 14. In this manner, the end 28 of mandrel 18 is received in and affirmatively engages the implant 14 to detachably mount implant 14 to applicator 12. Applicator 12 is provided with means for preventing relative rotational movement between the implant 14 and applicator 12 comprised, in the preferred embodiment shown, of a plurality of radially spaced, longitudinal slots 36 in the end 28 of mandrel 18 communicating with the longitudinal bore 20 therethrough and the wedge-shaped end 24 of piston 22. When piston 22 is forced down into the bore 20 in mandrel 18, the pointed end 24 of piston 22 acts to spread, or force the portions 38.of the threaded end of mandrel 18 between slots 36 outwardly into increasingly tighter frictional engagement with the interior wall of the bore 34 of implant 34, thereby preventing relative rotational movement of the implant 14 and applicator 12.

Implant 14 is formed in the shape of a generally elongate cylinder with a blunt, or rounded end 40 and the end 42 having the aforementioned bore 34 opening therein. The diameter of the ends 40 and 42 is smaller than the diameter of the middle portion 44 of the implant for a purpose to be explained below. The outside surface of implant 14 is provided with threads 46, the function of which are also set out below. Implant 14 is preferably constructed of any durable, relatively biologically inert substance such as carbon fiber, titanium, several medical grade hard plastics, and such other materials as are known in the art for use in such implants.

Figure 4:
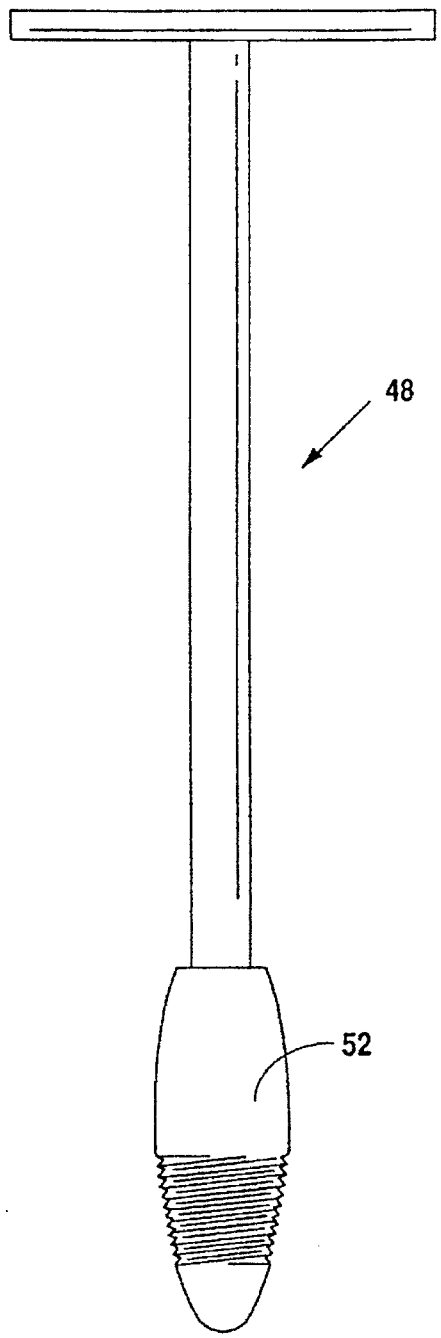
FIG. 4 is a plan view of a spreader which is used to advantage in connection with the insertion of the implant of the stabilizer of FIG. 1 between two adjacent vertebrae of a patient's spinal column.
Figure 6:
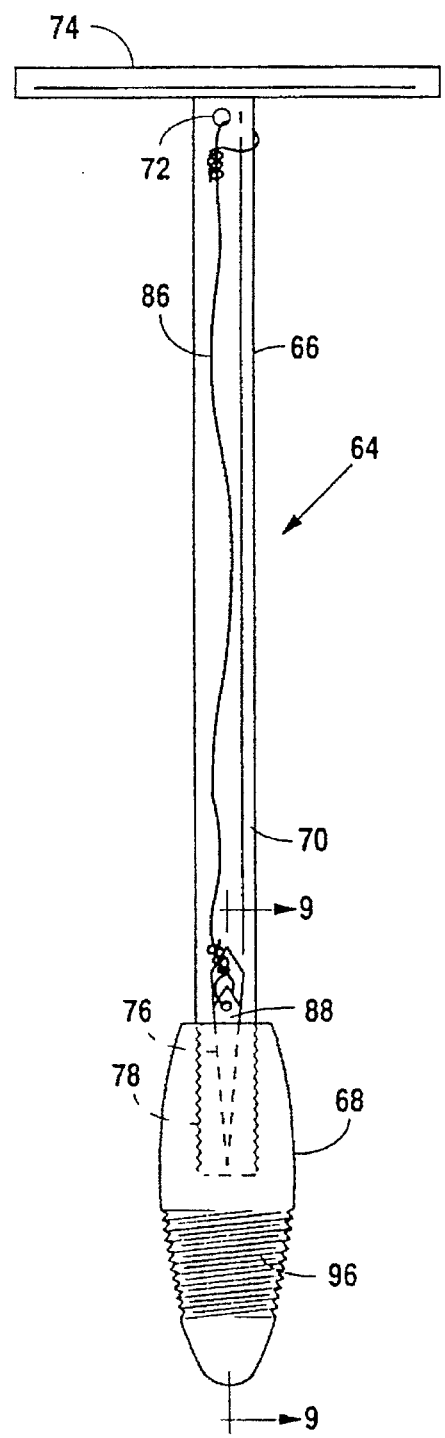
FIG. 6 is a plan view of a second embodiment of a stabilizer constructed in accordance with the present invention.
Figure 5:
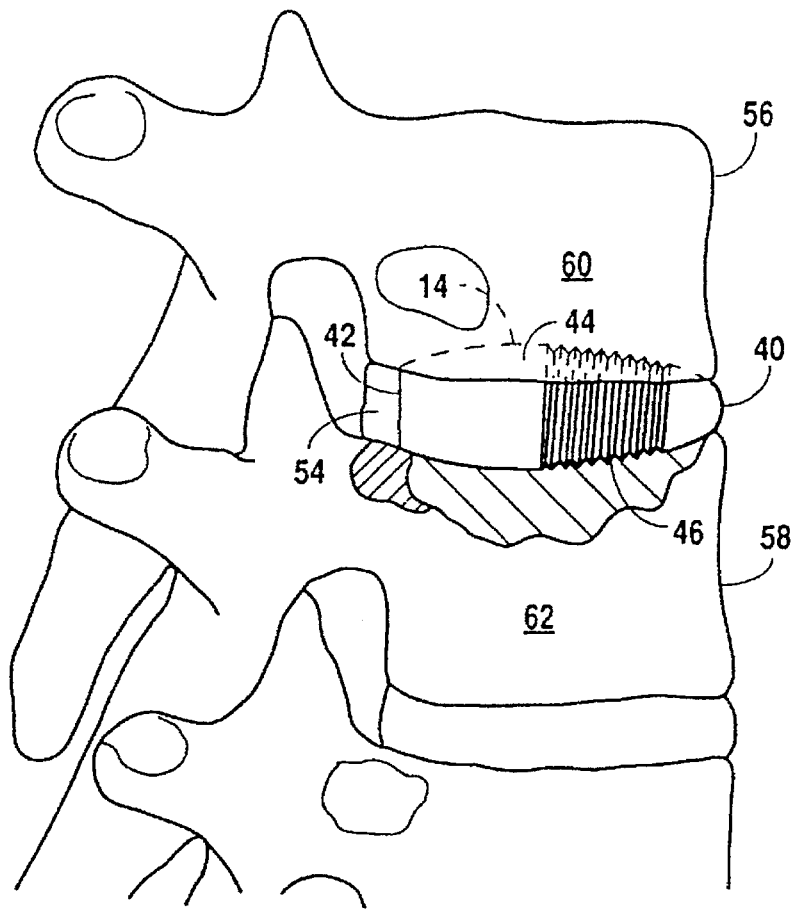
FIG. 5 is a lateral view of a portion of a human spinal column having the implant of the stabilizer of FIG. 1 inserted therein and having a portion of the bodies of the vertebrae adjacent the implant cut away to show the engagement of the vertebral bodies by the implant.
Figure 9:
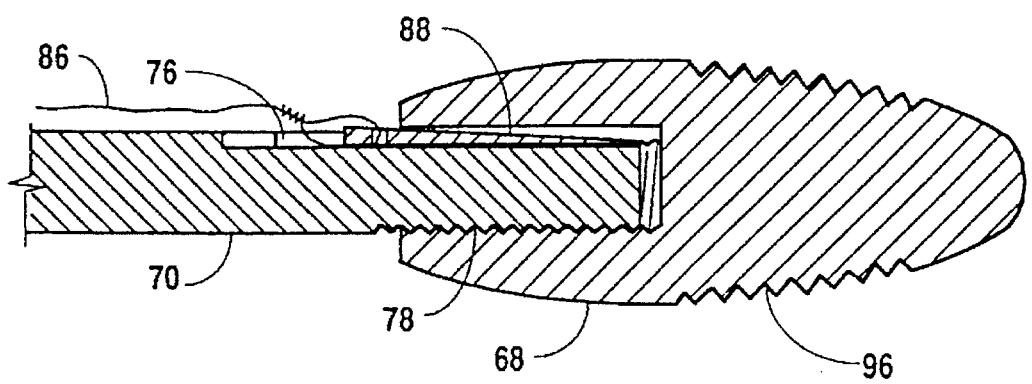
FIG. 9 is a longitudinal, sectional view of a portion of the stabilizer of FIG. 6, taken along the lines 9—9 in FIG. 6.

Referring now to FIGS. 4 and 5, there is shown a spreader, indicated generally at reference numeral 48, having integral handle 50 and implant 52 portions sized and generally shaped in the same size and dimensions as the stabilizer 10. The use of the stabilizer 10 of the present invention in, for instance, a method of lumbar intervertebral disk stabilization, or "LIDS", is illustrated in FIG. 5. Surgery is performed as in a simple diskectomy and the intervertebral disk 54 is exposed through a small laminotomy. The disk material is removed and any nerve root compression is corrected. The posterior longitudinal ligament and disk cartilage are removed until the surfaces of the bodies 60 and 62 of adjacent vertebrae 56 and 58, respectively, are exposed above and below the disk space.

Using the spreader 48, the vertebrae 56 and 58 are distracted to open the disk space, and once the desired "spread" has been achieved, the middle portion of the disk space is packed with cancellous bone chips (not shown). As described below, a kit of several spreaders, each having progressively larger diameter implant portions, is used to achieve the desired spread. Because the posterior longitudinal ligament is left intact to the opposite side and to the center of the disk space, the bone chips are held in place in the disk space. The appropriately-sized implant 14 of stabilizer 10 is then inserted into the disk space using the applicator 12 until the threads 46 formed on the outside surface of implant 14 engage the bodies 60 and 62 of the adjacent vertebrae 56 and 58, respectively. Piston 22 is then wedged into the bore 20 to cause the applicator 12 to frictionally engage implant 14 to prevent relative rotational movement therebetween and the stabilizer 10 is rotated. Rotation of the implant 14 in the disk space causes the threads 46 to bear against the bodies 60 and 62 to move the implant further into (or back out of, depending upon the direction of rotation) the disk space in an anterior-posterior direction so as to enable the implant 14 to be positioned in the disk space at a position in which the expanded, or larger diameter portion 44 and the smaller diameter ends 40 and 42 of implant 14 contact the respective lower and upper surfaces of the bodies 60 and 62 of the adjacent vertebrae 56 and 58. The respective lower and upper surfaces of the vertebral bodies 60 and 62 are slightly concave such that the expanded middle portion 44 of implant 14 allows the implant 14 to engage substantially more of the respective surfaces of the vertebral bodies 60 and 62 than conventional prosthetic devices, thereby providing increased stability to the fusion.

Once positioned in the disk space so as to provide maximum stabilization, pressure on the piston 22 is released and the piston 22 is backed out of the bore 34 so as to allow the applicator 12 to be rotated without rotating the implant 14. The applicator is then detached from the implant 14 by unscrewing and backed out of the incision in the patient. If necessary, a small amount of a physiologically compatible adhesive of a type known in the art is applied over the cancellous bone chips just medial to the implant to close off the remaining portion of the opening into the disk space. The patient should be able to ambulate soon after the LIDS procedure because of the stability imparted to the spinal column by the implant of the present invention. Before narrowing of the disk space occurs, the cancellous bone chips will have started the fusion process.

The stabilizer 10 is also used to advantage to perform, for instance, a posterior lateral intertransverse fusion. The implant 14 is inserted into the region of the disk space from which a portion of the disk has been removed as described above and the posterior lateral fusion performed. Because the implant 14 provides stability to the spine until the posterior lateral fusion is solid, the patient is generally able to ambulate soon after surgery. This procedure also prevents the narrowing of the disk space, which is a common problem with posterior lateral fusion.

Removal of the implant 14 is accomplished with relative ease compared to conventional implants. The mandrel 18 of applicator 12 is screwed back into the threaded bore 34 in implant 14, piston 22 is re-inserted into the longitudinal bore 20 in applicator 12, and by applying pressure to piston 22 to prevent relative rotation between implant 14 and applicator 12, the implant is simply rotated so as to cause posteriorly-directed movement of the implant 14 out of the disk space.

Referring now to FIGS. 6–9, an alternative embodiment of the stabilizer of the present invention is indicated generally at reference numeral 64. Stabilizer 64 is comprised of applicator 66 and implant 68 portions having the same general function and component parts as those of the stabilizer 10 shown in FIGS. 1–5. However, the mandrel 70 of applicator 66, rather than being provided with a bore having a piston disposed therein as with the bore 20 and piston 22 of the stabilizer 10, is provided with a hole 72 near the end in which the handle 74 is formed and a longitudinal groove 76 crossing the threads 78 formed in the end of mandrel 70 which is received by the threads 80 in the bore 82 of implant 68. A similar groove 84, best shown in FIG. 9, runs longitudinally across the threads 80 in the bore 82 of implant 68. A safety line, or wire, 86 is threaded through the hole 72 in mandrel 70 having a wedge-shaped key 88 attached to the other end thereof, and when the implant 68 is mounted to the mandrel 70 of applicator 66 and the grooves 76 and 84 aligned, key 88 is wedged into the key slot formed by the aligned grooves 76 and 84 by insertion into the portion 90 of the groove 76 formed at the end of the mandrel 70 which extends beyond the smaller diameter end portion 92 (compared to the diameter of the expanded middle portion 94) of implant 68, the applicator 66 and implant 68 are locked up to prevent relative rotation therebetween so that the threads 96 formed on the external surface of implant 68 function in the same manner and for the same purpose as described in connection with the stabilizer 10.

In certain applications, for instance, when fusion is being performed on a patient having deteriorating vertebrae, it may be desirable to have threads formed at more than one location on the external surface of the implant. In such circumstances, an implant such as the implant indicated at reference numeral 98 in FIG. 10 is utilized in connection with the applicator 12 shown in FIGS. 1–5 (those skilled in the art who have the benefit of this disclosure will recognize that the implant 98 could also be provided with a groove such as the groove 84 in the implant 68 of FIGS. 6–9 for use in connection with the applicator 66). Implant 98 is provided with two sets of threads 100 formed on the external surface thereof to increase the likelihood that the threads 100 will bear against the bodies of the vertebrae between which it is inserted to facilitate the anterior-posterior positioning of the implant 98 in the anatomical region of the disk space.

Figure 11:
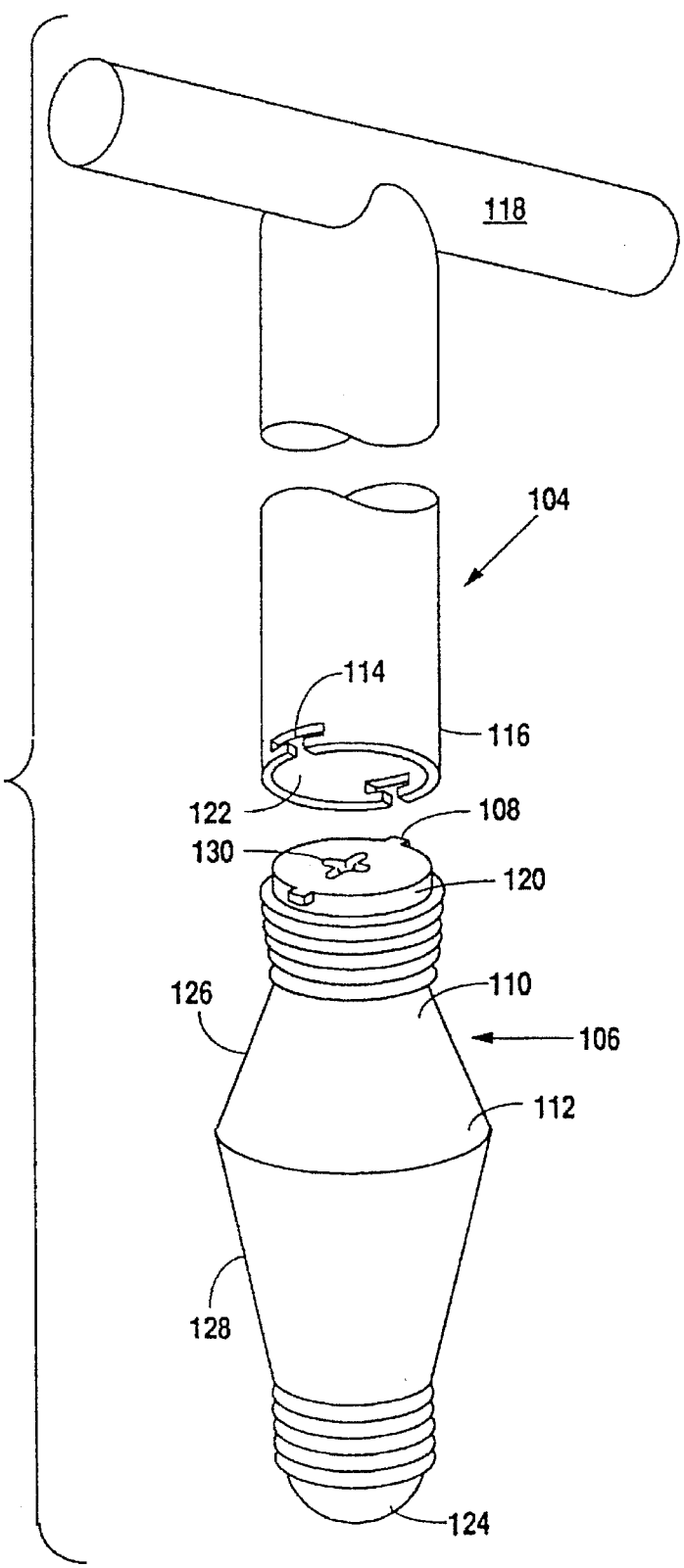
FIG. 11 is an exploded, projected view of a third embodiment of a stabilizer constructed in accordance with the present invention.

Referring now to FIG. 11, there is shown yet another embodiment of a disk stabilizer, indicated generally at reference numeral 102, constructed in accordance with the present invention. Stabilizer 102 is comprised of an applicator 104 and implant 106, implant 106 being detachably mounted to applicator 104 by receipt of the keys 108 formed in the smaller diameter end portion 110 (compared to the expanded middle portion 112) of implant 106 by the T-slots 114 formed at the end of the mandrel 116 of applicator 104 opposite handle 118. To provide additional rigidity to the mounting of implant 106 to applicator 104, the end 110 of implant 106 is provided with a cylindrical extension 120 which is received within a similarly dimensioned cavity 122 formed on the end of mandrel 116, the external surface of extension 120 bearing against the inside wall of the cavity 122 to stabilize the implant 106 on the end of applicator 104.

Implant 106 is, like each of the implants 16, 68, and 98, formed in the shape of a generally elongate cylinder having end 110 and 124 and middle 112 portions, the diameter of the middle portion 112 being larger than the diameter of the end portions 110 and 124. In the case of the implant 106, however, both ends 110 and 124 are provided with threads on the external surface of the implant and the larger diameter middle portion 112 is not located in equidistant from the ends 110 and 124. Instead, the largest diameter of the implant 106 is located closer to the end 110 of the implant 106 which is located posteriorly when inserted into the disk space such that the slope of the external surface 126 between the largest diameter of the middle portion 112 and end 110 is greater than the slope of the external surface 128 of implant 106 between the middle portion 112 and end 124. By shaping implant 106 in this manner, the increased slope of the surface 126 helps to prevent undesirable posterior movement of the implant 106 in the disk space once inserted. To decrease any tendency of the implant 106 to move in the anterior direction, the diameter of the end portion 124 of implant 106 is optionally larger than the diameter of the end portion 110. As is the case with each of the implants 16, 68, and 98, the end 124 of implant 106 is formed in a blunt, or rounded, shape to reduce the likelihood of injury to the nerves of the spinal cord during insertion into the disk space. To further facilitate proper anterior-posterior positioning of the implant 106 in performing the above-described LIDS procedure, the surface of the extension 120 at the end 110 of implant 106 is provided with a slot 130 for receiving a screwdriver blade (not shown) for fine adjustment of the position in the disk space.

Figure 12:
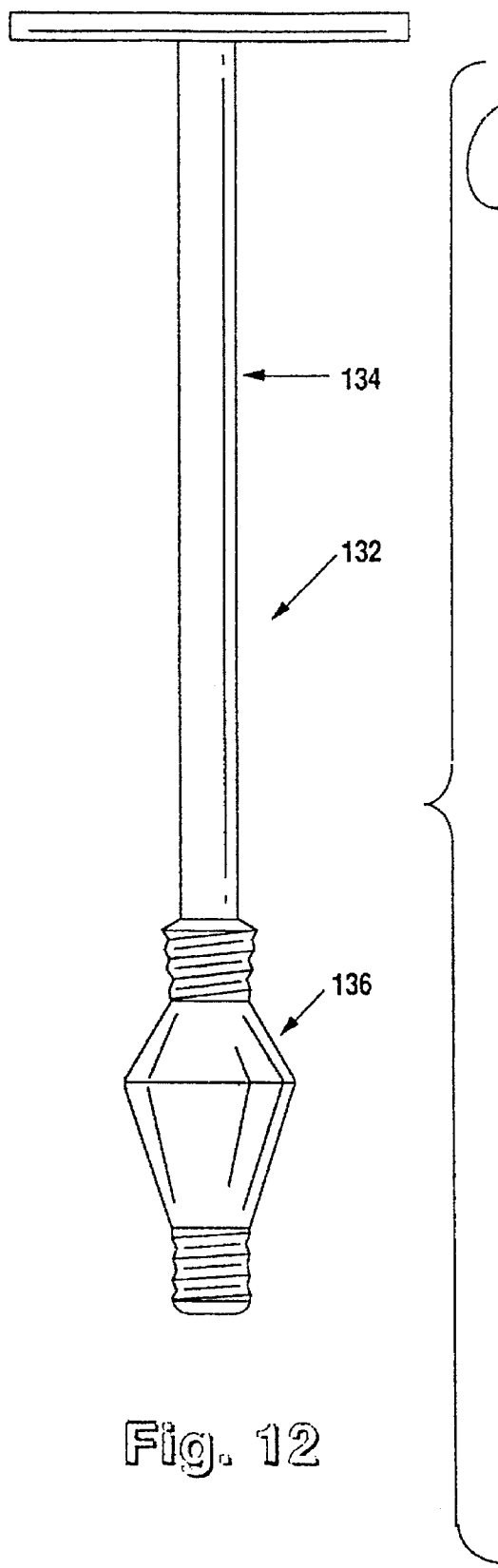
FIG. 12 is a plan view of a spreader which is used to advantage in connection with the insertion of the implant of the stabilizer of FIG. 11 between two adjacent vertebrae of a patient's spinal column.

In the same manner as the spreader 48 shown in FIG. 4, a spreader, indicated generally at reference numeral 132 in FIG. 12, is provided for spreading the adjacent vertebrae for insertion of the implant 106. Spreader 132 is formed of an integral handle 134 and implant portion 136, the latter being formed in the same approximate shape as the implant 106 of stabilizer 102. Those skilled in the art who have the benefit of this disclosure will recognize that it is advantageous to provide a kit comprised of a number of spreaders 48 or 132, depending upon the particular stabilizer 10, 64, or 102 being employed, of progressively larger diameters to obtain the desired degree of spread of the vertebrae adjacent the disk space into which the implant 14, 68, 98, or 106 is to be inserted. The kit of spreaders are of increasingly larger diameters in their respective expanded middle portions; it is also advantageous to supply spreaders in the kit having implant portions of different lengths. Likewise, it is advantageous to include in the kit implants of different diameters and lengths to obtain the best fit between the anatomical region of the disk space into which the implant is being inserted and the shape of the implant so as to be able to position the implant in the disk space at which the largest proportion of the external surface of the implant bears against the surfaces of the bodies of the adjacent vertebrae, thereby maximizing the stabilizing properties of the implant.

Although described in terms of the several embodiments shown in the figures, those embodiments are shown to exemplify the present invention, it being recognized by those skilled in the art that certain changes can be made to the specific structure of these various embodiments shown and described without departing from the spirit of the present invention. For instance, there are many ways other than those illustrated to mount the implant to the applicator so as to selectively prevent relative rotation therebetween while still enabling the applicator to be detached from the implant once positioned in the disk space, and all such structure is intended to fall within the scope of the present invention.

Likewise, the implant is described herein as being "generally cylindrical" in shape, but it is not expected that the present invention would be limited to implants having a circular cross-sectional shape because it is recognized that additional stability may be obtained by forming the implant with a slightly ovoid, or elliptical, cross-sectional shape while retaining the elongate, generally cylindrical shape of the implant. In the case of an implant such as is contemplated in the case of the stabilizer of FIGS. 1–5 but having a "flattened"0 cross-sectional shape, it will be recognized that the grooves 76 and 84 in the applicator 66 and implant 68, respectively, are aligned with both the handle 74 of applicator 66 and either the minimum or the maximum dimension of the cross-sectional shape of the implant to facilitate rotation of the implant in the disk space so as to enable the maximum surface area of the implant (e.g., the "flattened" surface) to bear against the bodies of the respective adjacent vertebrae. All such modifications, and other modifications which do not depart from the spirit of the present invention, are intended to fall within the scope of the following claims.

What is claimed is:

1. A method of intervertebral disk stabilization comprising the steps of:
   spreading adjacent vertebrae;
   removing a portion of the intervertebral disk from between the adjacent vertebrae;
   inserting an elongate, generally cylindrically shaped implant having middle and end portions, the middle portion being an expanded larger diameter than the end portions, into the space between the adjacent vertebrae from which a portion of the disk has been removed; and
   rotating the elongate implant to cause threads formed on the outside surface thereof to bear against the adjacent vertebrae to move the implant in an anterior-posterior direction until positioned at a point between the adjacent vertebrae at which both the larger diameter middle portion and the smaller diameter end portions of the elongate implant engage the bodies of the adjacent vertebrae to stabilize the adjacent vertebrae relative to each other.

2. The method of claim 1 wherein the elongate implant is detachably mounted to an applicator for insertion into the space from which a portion of the disk has been removed.

3. The method of claim 2 additionally comprising detaching the applicator from the elongate implant.

4. The method of claim 2 wherein the elongate implant is mounted to the applicator on threads and the applicator is detached from the elongate implant by rotating the applicator relative to the elongate implant after insertion of the elongate implant.

5. The method of claim 4 additionally comprising rotating the applicator to position the elongate implant.

6. The method of claim 5 additionally comprising preventing relative rotation of the elongate implant and the applicator during the positioning of the elongate implant.

7. The method of claim 1 additionally comprising preventing anterior-posterior movement of the elongate implant after the elongate implant is positioned.

8. The method of claim 1 wherein the adjacent vertebrae are spread by inserting a spreader comprised of a handle and an integral implant portion, the implant portion of the spreader being shaped in a similar shape to the elongate implant, between the adjacent vertebrae.

9. A method of intervertebral disk stabilization comprising the steps of:
   spreading adjacent vertebrae by inserting a spreader comprised of a handle and an integral implant portion between the adjacent vertebrae,
   removing a portion of the intervertebral disk from between the adjacent vertebrae;
   inserting the implant portions of additional spreaders between the adjacent vertebrae, each of the additional spreaders having implant portions of increasingly larger diameters, to spread the adjacent vertebrae progressively further apart;
   inserting an elongate, generally cylindrically-shaped implant having middle and end portions, the middle portion being an expanded larger diameter than the end portions, into the space between the adjacent vertebrae from which a portion off the disk has been removed, the implant portions of the respective spreaders being shaped in a shape similar to the elongate implant; and
   rotating the elongate implant to cause threads formed on the outside surface thereof to bear against the adjacent vertebrae to move the implant in an anterior-posterior direction until positioned at a point between the adjacent vertebrae at which both the larger diameter middle portion and the smaller diameter end portion of the elongate implant engage the bodies of the adjacent vertebrae to stabilize the adjacent vertebrae relative to each other.

10. The method of claim 9 additionally comprising preventing movement of the implant in an anterior or posterior direction in the disk space after the implant is positioned.

11. A method of intervertebral disk stabilization comprising the steps of:
    removing a portion of the intervertebral disk from between adjacent vertebrae;
    inserting a generally cylindrically-shaped implant comprised of middle and end portion having threads formed on the surface thereof into the space between the adjacent vertebrae from which the portion of the disk has been removed, the middle portion of the implant having an expanded larger diameter than the end portions of the implant;
    rotating the implant to cause the threads to bear against the adjacent vertebrae to cause the implant to move back and forth in the space between the adjacent vertebrae to position the implant at a point at which both the middle and end portions of the implant engage the adjacent vertebrae to stabilize the adjacent vertebrae relative to each other.

12. The method of claim 11 wherein the implant is attached to an applicator for insertion into the disk space and then detached from the applicator after the implant is positioned in the disk space.

13. The method of claim 12 additionally comprising rotating the applicator to position the implant.

14. The method of claim 13 additionally comprising preventing rotation between the implant and the applicator until after the implant is positioned in the disk space.

15. The method of claim 14 additionally comprising preventing movement of the implant in the anterior or posterior direction after the implant is positioned in the disk space.

16. The method of claim 11 additionally comprising spreading the adjacent vertebrae before inserting the implant into the disk space.

* * * * *